United States Patent [19]

Ewers et al.

[11] Patent Number: 4,770,860

[45] Date of Patent: Sep. 13, 1988

[54] POROUS HYDROXYL APATITE MATERIAL

[75] Inventors: Rolf Ewers, Graf-Spee-Str. 46, D-2300 Kiel 1; Christian Kasperk, Kiel, both of Fed. Rep. of Germany

[73] Assignee: Rolf Ewers, Fed. Rep. of Germany

[21] Appl. No.: 95,066

[22] PCT Filed: Dec. 3, 1986

[86] PCT No.: PCT/EP86/00702

§ 371 Date: Sep. 16, 1987

§ 102(e) Date: Sep. 16, 1987

[87] PCT Pub. No.: WO87/03491

PCT Pub. Date: Jun. 18, 1987

[30] Foreign Application Priority Data

Dec. 3, 1985 [DE] Fed. Rep. of Germany ....... 3542744

[51] Int. Cl.$^4$ ................................................. C01F 5/02
[52] U.S. Cl. ..................................... 423/173; 423/164

[58] Field of Search ................................. 423/164, 173

[56] References Cited

U.S. PATENT DOCUMENTS

| 2,043,238 | 6/1936 | Curtis | 423/173 |
| 2,053,266 | 9/1936 | Curtis | 423/173 |
| 2,067,538 | 1/1937 | MacIntire | 423/173 |
| 2,143,025 | 1/1939 | Newton | 423/173 |
| 3,236,593 | 2/1966 | Hartmann | 423/173 |

Primary Examiner—Morton Foelak
Attorney, Agent, or Firm—Lowe, Price, LeBlanc, Becker & Shur

[57] ABSTRACT

A porous hydroxyl apatite material is disclosed which is made from calcium-rich basic skeletons of lime-encrusting algae converted into hydroxyl apatite and which serves for use as artificial bone, artificial tooth root, augmentation material, stabilization material, artificial hollow bodies or defect filling material.

5 Claims, No Drawings

POROUS HYDROXYL APATITE MATERIAL

The present invention relates to a porous hydroxyl apatite material and to the employment thereof in medicine, dentistry and veterinary medicine.

From U.S. Pat. No. 3,929,971, there is already known a synthetic, porous hydroxyl apatite material which has a special microstructure and which may be employed as a biomaterial, e.g. as a prosthesis material, bone implant and the like. This previously known hydroxyl apatite material is made from the carbonate skeletons of sea animals, in particular corals and starfish.

It is an object of the present invention to provide a novel porous hydroxyl apatite material which, because of the starting materials employed in its manufacture, has a special porosity and which exhibits a special form.

For this purpose, there serves the porous hydroxyl apatite material which is characterized in that the material is produced from the calcium-rich basic skeletons of lime-encrusting algae converted into the hydroxyl apatite material.

According to preferred embodiments of the invention, the pores of the porous hydroxyl apatite material are filled with a re-absorbable or a bone-inducing material such as bone marrow.

The porous hydroxyl apatite material according to the invention is useful, in particular, as artificial bone, artificial tooth root, stabilizing material, artificial hollow bodies, supplementary material, lining material or defect-filling material.

For the production of the hydroxyl apatite material, according to the invention all algae, and in particular those from the littorals and sub-littorals of the oceans, in particular species of Corallinaceae such as *Corallina officinalis, Corallium, rubens, Lithothamion calcarum* and species of Codiaceae, e.g. Halimeda spec., including benthish crust-forming algae such as Lithothamnion spec. and Lithophyllum spec. can be used, which, in general, encrust lime, even if only to a small extent.

In order to obtain the lime skeletons of the algae, the organic components of the algae must firstly be removed. This can be effected by so-called "maceration". For this purpose, for example, vital or dried algae material can be treated with copper complex salts, e.g. Schweizer's reagent or with lithium chloride or bromide solutions, or subjected to pyrolysis. Such maceration processes, i.e. methods of treatment for removing the organic material, are likewise described in the aforesaid U.S. Pat. No. 3,929,971, e.g. submersion in dilute sodium hypochlorite solutions.

Following the maceration by means of Schweizer's reagent or lithium chloride solution, or after pyrolysis, the remaining calcium carbonate basic material, freed of organic substance and existing in granular form, is thoroughly washed with distilled water. The grain size of the material is between 0.1 and 2 millimeters.

The calcium-rich basic skeleton obtained from the algae is then converted into hydroxyl apatite in a known manner. This conversion into hydroxyl apatite is usually effected by a hydrothermal process or by the use of a phosphate salt bath. For this purpose, alkali metal phosphates such as sodium orthophosphate, potassium orthophosphate and ammonium orthophosphate, acidic phosphates and phosphate mixtures may be employed. Likewise, orthophosphoric acids may also be employed for this purpose. This hydrothermal treatment for converting calcium carbonate into hydroxyl apatite is likewise disclosed in the aforesaid U.S. Pat. No. 3,929,971. The hydrothermal treatment is carried out in the usual way at high pressure and at high temperature.

An example for such a treatment comprises maintaining the porous, macerated granules of lime-encrusting algae with sodium hydrogen phosphate and doubly-distilled water in proportions of 1:1:4 in a closed container for two to three days under the following conditions:
  (a) 300° C. and 500 bar; or
  (b) 600° C. and 1000 bar.

Depending upon the physical conditions employed, an influence can be exerted on the re-absorbability of the material in bone surgery.

After the hydrothermal treatment, the hydroxyl apatite material usually exhibits a granular form. From this granular form, compact pieces can be produced by agglomeration, e.g. by conventional sintering methods, if required under the application of pressure and with the addition of conventional sinter-promoting materials.

For agglomeration of the granular material into compact pieces, the granular material is firstly pressed into molded bodies and after a pre-heating phase of approximately 4 hours, these are then roasted at a temperature of 1000° to 1400° C. for 4 to 5 hours, and subsequently cooled, e.g. over 4 to 5 hours. For deliberately affecting the size of the pores of the hydroxyl apatite bodies after sintering, the sintering is carried out with the addition of an empirically determined amount of $H_2O$ (double-distilled).

The pores of the hydroxyl apatite material according to the invention may be filled with re-absorbable materials. In that way, the compatibility of the hydroxyl apatite material in utilization in medicine, dentistry or veterinary medicine can be improved, and in particular the infection rate occurring with the hydroxyl apatite material by the filling of the pores can be lowered and/or the bone induction can be increased. As re-absorbable materials, lyophilisized heterologous collagen filaments, homologous lyophilized fibrin, gypsum, proteins such as marrow or polylactic acid preparations, e.g. polydioxanones, may be employed.

An advantage of an embodiment of the hydroxyl apatite material according to the invention, in comparison to the hydroxyl apatite material which was manufactured from coral material in accordance with U.S. Pat. No. 3,929,971, lies in the granular form, which for certain possible applications provides advantages.

We claim:

1. A porous hydroxyl apatite material, characterized in that the material is made from the calcium-rich basic skeletons of lime-encrusting algae converted into hydroxyl apatite.

2. A porous hydroxyl apatite material according to claim 1, characterized in that its pores are filled with a re-absorbable material.

3. A porous hydroxyl apatite material according to claim 1, characterized in that its pores are filled with a bone-inducing material.

4. A porous hydroxyl apatite material according to claim 3, characterized in that its pores are filled with bone marrow.

5. Use of the porous hydroxyl apatite material according to one of claim 1 as artificial bone, artificial tooth root, augmentation material, stabilization material, artificial hollow bodies or defect-filling material.

* * * * *